US00RE39871E

(19) United States
(12) Reissued Patent
Skardon

(10) Patent Number: US RE39,871 E
(45) Date of Reissued Patent: Oct. 9, 2007

(54) PARTICULATE DETECTION AND AIR ADVICE PROVISION

(75) Inventor: John N. Skardon, Vancouver, WA (US)

(73) Assignee: AirAdvice, Inc., Portland, OR (US)

(21) Appl. No.: 11/129,743

(22) Filed: May 13, 2005

Related U.S. Patent Documents

Reissue of:
(64) Patent No.: 6,693,546
Issued: Feb. 17, 2004
Appl. No.: 10/205,825
Filed: Jul. 26, 2002

U.S. Applications:

(63) Continuation of application No. 09/387,041, filed on Aug. 31, 1999, now Pat. No. 6,466,133.

(51) Int. Cl.
*G08B 21/00* (2006.01)

(52) U.S. Cl. ..... 340/627; 340/601; 340/603; 340/607; 340/870.2; 340/539.26; 340/539.28; 340/539.29; 340/539.12; 340/517; 706/930; 702/23; 702/29

(58) Field of Classification Search ..... 340/607, 340/601, 603, 870.92, 627, 539.26, 539.28, 340/539.29, 539.12, 517
See application file for complete search history.

(56) References Cited

U.S. PATENT DOCUMENTS 4,249,244 A * 2/1981 Shofner et al.
4,420,256 A * 12/1983 Fladda et al.
5,001,463 A * 3/1991 Hamburger
5,394,934 A * 3/1995 Rein et al.
5,428,964 A * 7/1995 Lobdell
5,549,117 A * 8/1996 Tacklind et al.
5,553,006 A 9/1996 Benda (Continued)

OTHER PUBLICATIONS

William F. Lyon, Ohio State University Extension Facsheet; Entomology, "House Dust Mites," reprinted Feb. 26, 1998, pp. 1–4.*

(Continued)

*Primary Examiner*—Julie Bichngoc Lieu
(74) *Attorney, Agent, or Firm*—Schwabe Williamson & Wyatt

(57) ABSTRACT

A novel basic allergen/particulate data collection device and a novel multi-function personal air quality management device are disclosed. Both devices include sensor sub-assembly detecting and reporting on allergen/particulate data (preferably, for allergen/particulate with sizes smaller than 5 micron) for an indoor location (where the asthma patient is situated). Both devices are communication enabled to allow the allergen/particulate data to be provided to an air/asthma advice server, to generate air/asthma advice for an asthma patient, taking into consideration the allergen/particulate data as well as air quality data for a surrounding outdoor area of the indoor location. In one embodiment of the basic device, the communication interface is tailored for "harsh environment" local area networking. When combined with its streamlined functionality, the device is particularly suitable (especially in terms of economics) for multiple deployment (along with a "base station"), such as in the case of an home application. In one embodiment of the multi-function device, the communication interface is tailored for "controlled environment" wide area networking. When combined with its rich functionality, the device is particularly suitable for standalone deployment, such as in the case of a professional application. Various alterations and modifications of different embodiments are also disclosed.

45 Claims, 7 Drawing Sheets

U.S. PATENT DOCUMENTS

| | | | | | |
|---|---|---|---|---|---|
| 5,589,824 | A | * | 12/1996 | Lynch | |
| 5,626,144 | A | * | 5/1997 | Tacklind et al. | |
| 5,646,597 | A | * | 7/1997 | Hamburger et al. | |
| 5,704,366 | A | * | 1/1998 | Tacklind et al. | |
| 5,732,709 | A | * | 3/1998 | Tacklind et al. | |
| 5,786,767 | A | * | 7/1998 | Severino | |
| 5,831,876 | A | * | 11/1998 | Orr et al. | |
| 5,848,378 | A | * | 12/1998 | Shelton et al. | |
| 5,892,690 | A | | 4/1999 | Boatman | |
| 6,023,223 | A | * | 2/2000 | Baxter, Jr. | |
| 6,078,853 | A | * | 6/2000 | Ebner et al. | |
| 6,114,964 | A | * | 9/2000 | Fasano | |
| 6,288,646 | B1 | * | 9/2001 | Skardon | 340/627 |
| 6,317,639 | B1 | * | 11/2001 | Hansen | 700/83 |
| 6,336,900 | B1 | * | 1/2002 | Alleckson et al. | 600/485 |

OTHER PUBLICATIONS

"Model 1060 Features and Specifications," http://www.ppmcorp.com/products/hh60spec.html, reprinted Mar. 8, 1999, 1 page.*

Joel Johnson and Gerry Flanagan, "Real–Time Dust Monitoring provides Data on Aerosols and Particulates," reprinted from Industrial Hygiene News, 2 pages.*

"Model 1060 Handheld Aerosol Monitor with Detached Sensor," http://www.ppmcorp.com/products/hh60desc.html, reprinted Mar. 8, 1999, 1 page.*

"Model 1010 Handheld Aerosol Monitor," http://www.ppmcorp/hh05desc.html, reprinted Mar. 8, 1999, 1 page.*

Health and Safety Application Note ITI–036, "Dusttrak™ Aerosol Monitor Theory of Operation, Revised Nov. 14, 1997," http://www.tsi.com/his/homepage/applnote/iti_036.htm, Copyright 1996 TSI Incorporated, reprinted Mar. 8, 1999, 2 pages.*

"Dusttrak™ Aerosol Monitor Model 8520, Features, Specification and Accessories," Revised Sep. 10, 1998, http://www.tsi.com/his/homepage/dusttrak/dustspec.htm, Copyright 1997 TSI Incorporated, reprinted Mar. 8, 1999, pp. 1–4.*

Opto–System project Team, ELECOM Group, Sharp Corporation, "Dust Sensor GP2U 5 Application Note," Nov. 28, 1997, pp. 2–14.*

Sharp Corporation, "GP2U06 High Sensitivity Dust Sensor," as of May 1997, 2 pages.*

* cited by examiner

PARTICULATE DETECTION AND AIR ADVICE PROVISION

Matter enclosed in heavy brackets [ ] appears in the original patent but forms no part of this reissue specification; matter printed in italics indicates the additions made by reissue.

This is a continuation of U.S. patent application Ser. No. 09/387,041 filed on Aug. 31, 1999, now U.S. Pat. No. 6,466,133.

BACKGROUND OF THE INVENTION

1. Field of the Invention

The present invention relates to the field of medical devices and advising systems. More specifically, the present invention relates to allergen detection and air or asthma related advising systems.

2. Background Information

Asthma is a chronic disease that affects among other things, the lung functions of a patient. It is estimated that 6% to 9% of the population of the developed world are affected, and the number of diagnosed cases is growing at 5% per year, ten times the rate of population growth. The number of newly diagnosed cases of pediatric asthma has the health authorities of many countries consider asthma to be an epidemic. In United States, about 15 millions American are affected, making it the sixth ranked chronic disease of the country. About 5,500 people die from asthma related complication each year. The annular medical cost is estimated to be $6 billion. In addition, thousands of work and school days are lost.

Lung irritants such as particulates, plants and animal allergens, and certain types of man-made pollution are the usual triggers leading to asthma attacks. Typically, they are 50 microns or smaller. In the home setting, recent research has determined that allergens can accumulate to levels 2×-10× higher than outside levels. More importantly, "respirable" particulates less than 5 microns in size are of particular concern to health authorities. Current asthma treatment guidelines typically advise a patient to, in order to priority, (1) prevent an attack by avoiding asthma triggers, (2) check their lung function regularly and (3) take medication when necessary.

Although prevention is a high priority or even preferred aspect of the treatment plan for a patient, currently, very limited help is available to assist a patient to avoid asthma triggers, especially in the home setting. This is because allergenic particles that are 50 microns or smaller in size are too small to see without a microscope. Much of the air monitoring devices known in the art are catered for commercial (i.e. workplace) use, designed to monitor industrial pollutants. U.S. Pat. Nos. 5,001,463 and 5,646,597 issued to Hamburger disclosed two allergen detection devices for triggering an alarm when allergen level exceeding certain predetermined threshold is detected. A filter, collection and detection arrangement is employed in the '463 patent, whereas the '597 patent improves on the optical detection of the 463 patent. However, both devices suffer from at least the following disadvantages:

(a) neither devices are designed to detect respirable allergens that are smaller than 5 microns, which as mentioned above, have recently been identified by medical research as among the most relevant allergens to avoid;

(b) both devices are only capable of generating an alarm based on the amount of allergens detected in the ambient air of the location of the monitoring device, which when located indoor, ignore the critical component of outdoor air quality (i.e. the air quality of the immediate outdoor area surrounding the indoor location);

(c) the vertical sampling arrangement requires the use of extensive filtering and purging system;

(d) the art ignores the role of humidity and temperature in the lung function;

(e) maintaining, including cleaning, and calibrating these devices are difficult, requiring extensive disassembly and instrumentation; and (f) no provisions are provided for storing and communicating the collected data.

Thus, an improved approach to allergen monitoring and air/asthma advice generation is desired.

3. Terminology

Throughout the remaining specification, including the claims, usage of the term "allergen" is intended to include particulates, plants and animal allergens, man-made pollution, and the like, and usage of the term "air/asthma advice" is intended to cover air quality and/or asthma related information, suggestion, counsel, guidance, recommendation, admonition, direction, instruction, alert, warning, and the like.

SUMMARY OF THE INVENTION

A sub-assembly for detecting and reporting on allergen data (preferably, for allergen with sizes smaller than 5 micron) is provided to a basic allergen data collection device as well as a multi-function personal asthma management device. Both devices are communication enabled, to allow the allergen data of the location where the device is situated (typically indoor), to be provided to an air/asthma advice server, that generates air/asthma advice for an asthma patient, taking into consideration allergen condition of a location as well as air quality of the surrounding area. In one embodiment of the basic model, the communication interface is tailored for "harsh environment" local area networking. In one embodiment of the multi-function model, the communication interface is tailored for "controlled environment" wide area networking.

BRIEF DESCRIPTION OF DRAWINGS

The present invention will be described by way of exemplary embodiments, but not limitations, illustrated in the accompanying drawings in which like references denote similar elements, and in which.

DETAILED DESCRIPTION OF THE INVENTION

Figure 1:
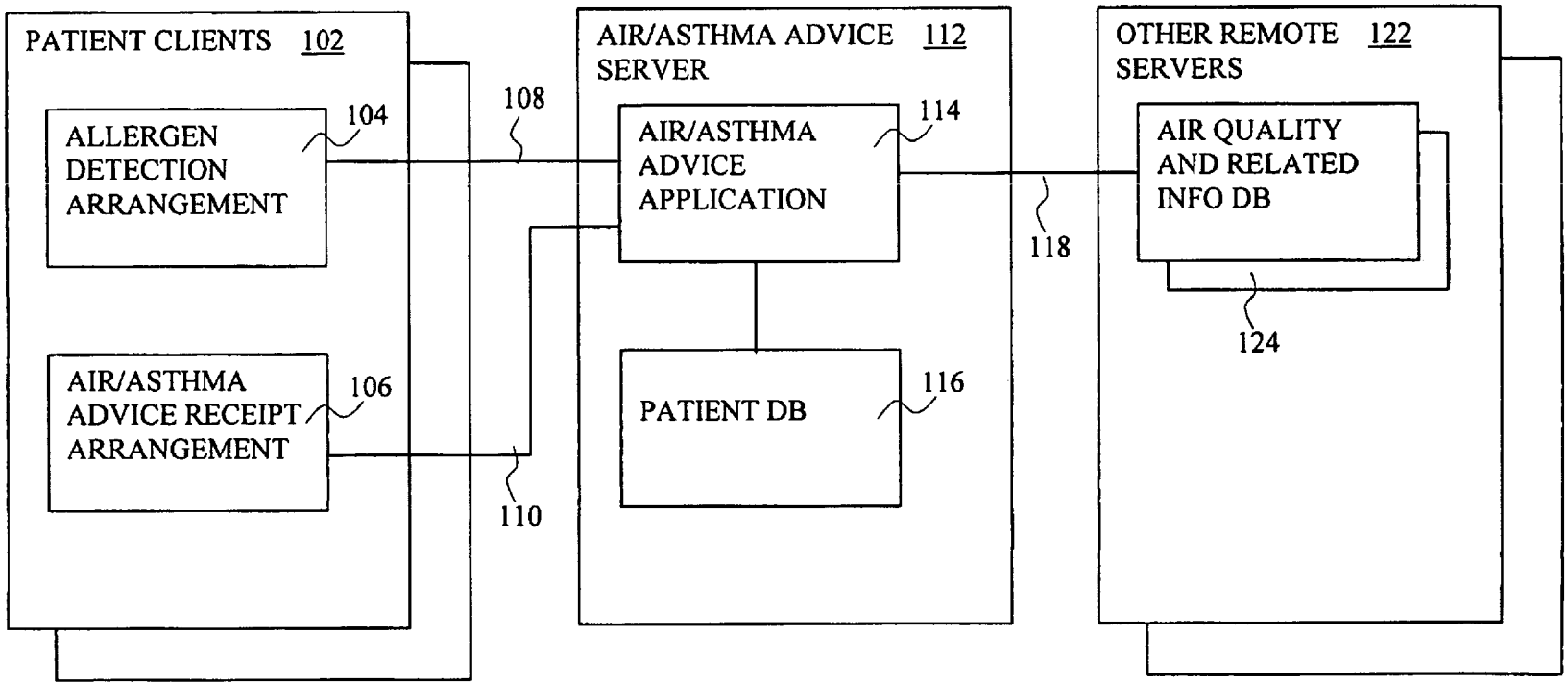
FIG. 1 illustrates an overview of the present invention in accordance with one embodiment.

In the following description, various aspects of the present invention will be described, and various details will be set forth in order to provide a thorough understanding of the present invention. However, it will be apparent to those skilled in the art that the present invention may be practiced with only some or all aspects of the present invention, and the present invention may be practiced without the specific details. In other instances, well known features are omitted or simplified in order not to obscure the present invention.

Parts of the description will be presented using terminology commonly employed by those skilled in the art to convey the substance of their work to others skilled in the art, including terms of operations performed by a computer system, and their operands, such as transmitting, receiving, retrieving, determining, generating, allergen data, air quality data, and the like. As well understood by those skilled in the art, these operands take the form of electrical, magnetic, or optical signals, and the operations involve storing, transferring, combining, and otherwise manipulating the signals through electrical, magnetic or optical components of a system. The term system includes general purpose as well as special purpose arrangements of these components, that are standalone, adjunct or embedded.

Various operations will be described as multiple discrete steps performed in turn in a manner that is most helpful in understanding the present invention. However, the order of description should not be construed as to imply that these operations are necessarily performed in the order they are presented, or even order dependent. Lastly, repeated usage of the phrase "in one embodiment" does not necessarily refer to the same embodiment, although it may. Referring now FIG. 1, wherein a block diagram illustrating an overview of the present invention in accordance with one embodiment is shown. As illustrated, for the particular embodiment, each patient client 102 is equipped with allergen detection arrangement 104, as well as air/asthma advice receipt arrangement 106. Both allergen detection and air/asthma advice receipt arrangements 104 and 106 are communicatively coupled to geographically removed air/asthma advice server 112; for the particular embodiment, through communication links 108 and 110 respectively. Air/asthma server 112 includes air/asthma advice application 114 and patient client database 116. Air/asthma advice server 112 in turn is also communicatively coupled to a number of other remote servers 122, through a communication link or links 118. Each of the other remote servers 122 includes at least air quality and other asthma related information databases 124.

Allergen detection arrangement 104 provided to each patient client 102 is used to detect allergen level at a location for the patient client 102, the location particular arrangement 104 is located. In a presently preferred embodiment, to be described more fully below, the allergens monitored are allergens with sizes smaller than 5 microns. Typically, a monitored location is a "fixed" indoor location, such as the "home" or the office of a patient client 102. The term "home" as used herein is intended to cover the primary as well as other temporary residence of a patient client 102, where the patient client 102 e.g. is an "invitee", such as someone else's home, a hotel, and so forth. As will be readily apparent from the description to follow, in alternate embodiments, a monitored location may also be simply a "substantially stationery" enclosed location, such as the patient client's automobile or a boat, to be described more fully below.

In accordance with the present invention, allergen detection arrangement 104 provides the detected allergen level at a monitored location to air/asthma server 112, more specifically, to air/asthma advice application 114 of server 112.

In response, air/asthma advice application 114 retrieves at least air quality data for a general area of the location monitored, e.g. in the earlier described case of a "fixed" indoor location, an outdoor area surrounding the indoor location being monitored. For the particular embodiment, air/asthma advice application 114 retrieves the air quality data from remote servers 122. Examples of air quality data include air pollution data (such as ozone, oxides of nitrogen, oxides of sulphur, photochemical smog), weather data (such as humidity, temperature, and barometric pressure), natural phenomenons (such as pollen level, occurrence of sandstorm, tornado, forest fire,), man made pollution events (such as agricultural burns) and so forth. Examples of remote servers 122 include publicly accessible servers of the Environmental Protection Agency (EPA) and National Weather Services of the United States Government, as well as network or cable news web servers, such as MSNBC.com and CNN.com. In alternate embodiments, air/asthma advice application 114 may further retrieve other asthma related information for the general area from additional other remote servers 122. Examples of other asthma related information and additional other servers 122 include asthma alerts or warning bulletins posted on free or subscription based servers of educational and research institutions of the like (such as servers of the National Center for Diseases, Harvard Medical School and so forth). In yet other alternate embodiments, air/asthma advice application 114 may cache some of the air quality and other asthma related data (e.g. the most frequently accessed data) on server 112, i.e. maintaining local copies of the data. For these embodiments, whenever local copies are available, air/asthma advice application 114 may retrieve from the local cache instead.

The size of the general area is dependent on the granularity of the air quality and other asthma related data being maintained by other servers 122. For examples, the size of the general area may be an area covered by the same zip code, or it may be an entire statistical metropolitan area, depending on whether the air quality data are maintained by other servers 122 by zip codes or by statistical metropolitan areas. The size of the general area may also be further application dependent. For example, even though the air quality data are available by zip codes, air/asthma application 114 may nevertheless treat all areas with the same m most significant zip code digits as the same general area.

Upon retrieving air quality (and optionally, other asthma related data), air/asthma application 114 generates air/asthma advice for each patient client 102, based at least in part on the allergen level data received from the patient client 102 for a monitored location and the retrieved air quality data for the surrounding general area of the monitored location. Thus, for the purpose of the present invention, as long as the companion outdoor air quality to be taken into consideration in the generation of air/asthma advice is considered invariant (as in the case of a statistical metropolitan area), a monitored location such as the interior space of the patient client's automobile or boat (when used on a routine "local" basis, as opposed to an exceptional long distance journey) is "substantially stationery", equivalent to that of a "fixed" location, as in the case of the patient's home or office.

For the particular embodiment, patient client database 116 stores medical as well as basic identification information for each of a number of patient clients 102. In generating air/asthma advice for each patient client 102, air/asthma application 114 further takes into consideration the relevant medical information maintained for the patient client 102. Similarly, what medical information is considered relevant and taken into consideration is also application dependent. That is, in a more sophisticated variation of the embodiment, more medical information may be taken into consideration, and in a less sophisticated variation of the embodiment, less medical information may be taken into consideration. In a most basic alternative embodiment, air/asthma application 114 may simply generate the air/asthma advice without taking into consideration the medical data of a patient client 102. Additionally, non-medical client data, such as location and construction of "home", proximity to sources of ambient air pollution (e.g. highways, power plants, chemical facilities, and so forth), may also be collected, and taken into consideration by air/asthma advice application 114.

Upon generating an air/asthma advice response in one of the above described manners, air/asthma advice application 114 provides the generated air/asthma advice response to the patient client 102 through the patient client's air/asthma advice receipt arrangement 106. The content of the advice response is application dependent, e.g. the response may be an indoor air quality advisory, an outdoor air quality advisory, a weather advisory and/or a natural/man made pollution event advisory. The advice response may be provided in any one of a number of forms, including but not limited to, a beeping signal, a paging message, a voice message, a fax message, an email, and so forth, so long it is consistent with the capability of the air/asthma advice receipt arrangement 106 provided to the particular patient client 102. Different types of receipt arrangement 106, and therefore, different advice response forms may be employed for different patient clients 102. Multiple receipt arrangements 106 may also be provided for one patient client 102. In alternate embodiments, the air/asthma advice responses may also be provided to the patient clients' parents, guardians, nurses or doctors, in lieu of or in addition to the patient clients.

Having now described an overview of the present invention, various embodiments of allergen detection arrangement 104 as well as air/asthma advice receipt arrangement 106 will be described in more detail below, along with communication link or links 108, referencing FIGS. 2a-2b and FIGS. 3a-3e. Similarly, one embodiment each of server 112, air/asthma application 114 and patient client database 116 will be described in more detail below, referencing FIGS. 4-6. As to remote servers 122, the examples described above adequately set forth their nature to practice the present invention. It is readily apparent from these examples., communication link or links 118 may be any one of a number of communication medium known in the art, including but not limited to the Public Switching Telephone Network (PSTN), the Integrated Service Digital Network (ISDN), a Frame Relay network, an Asynchronous Transfer Mode (ATM) network, or the Internet, depending on the requirement of remote servers 122 accessed. Accordingly, remote servers 122 and communication link or links 118 will not be further described.

Figure 2A:
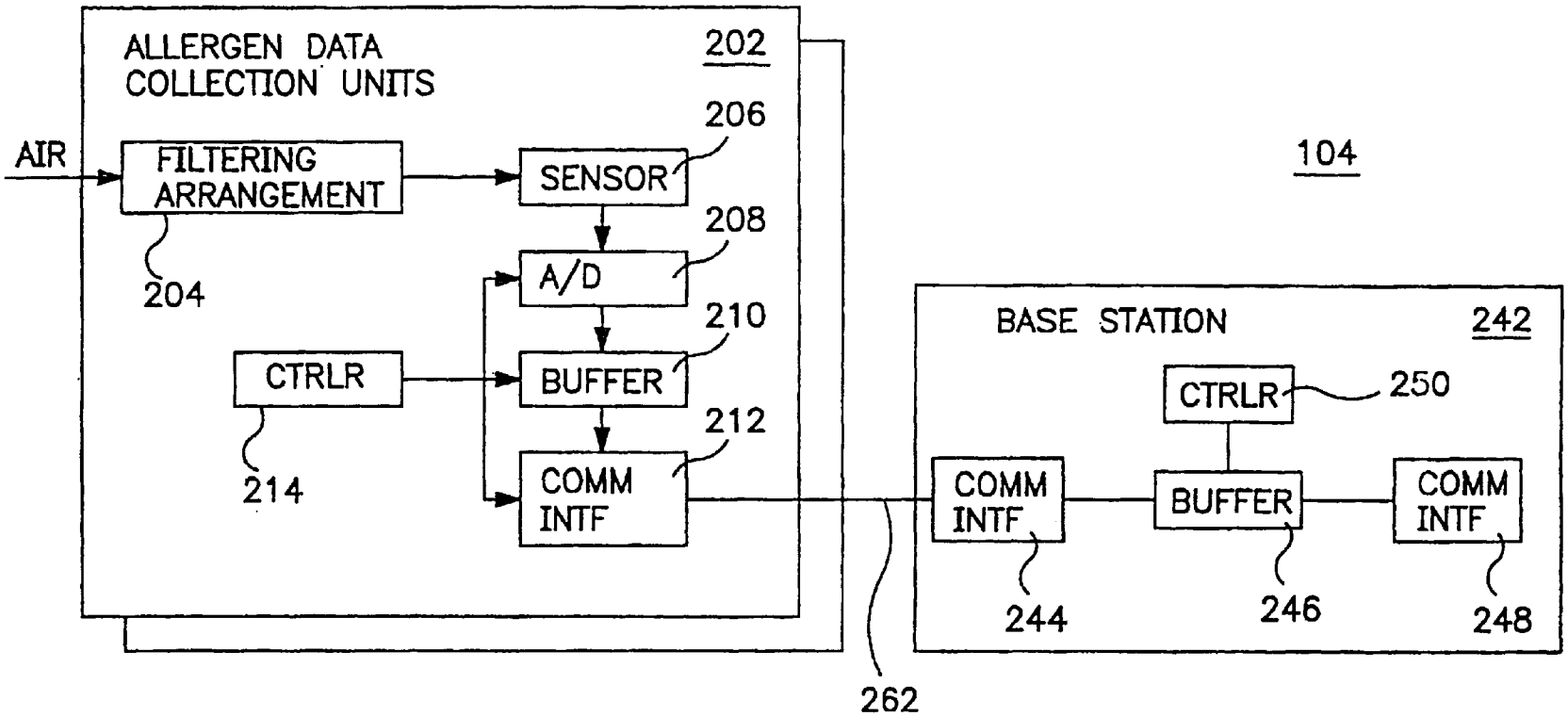
FIGS. 2a-2b illustrate allergen detection arrangement of FIG. 1 in further detail, in accordance with two embodiments.
Figure 2B:
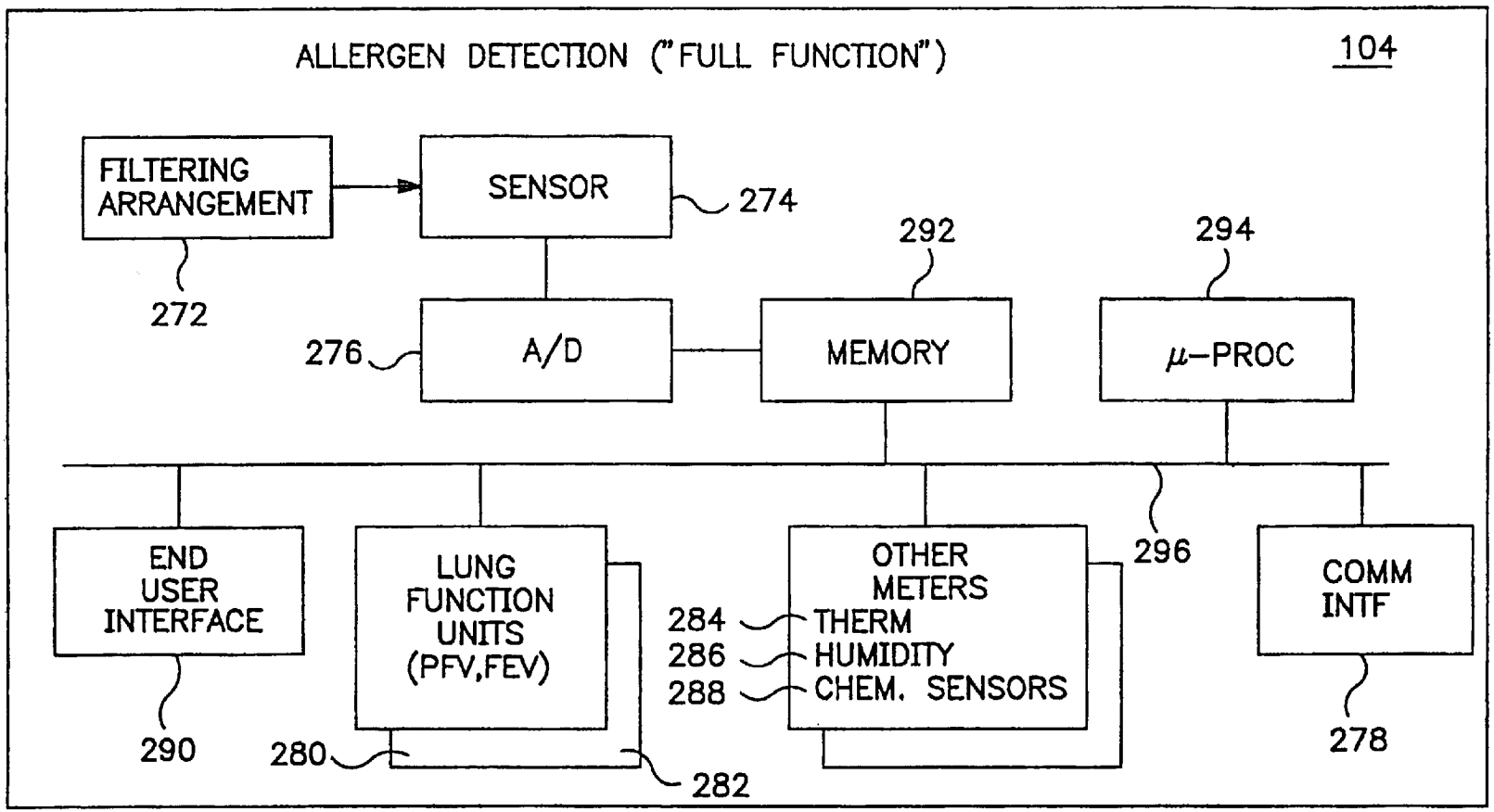

Referring now to FIGS. 2a-2b, wherein two block diagrams illustrating allergen detection arrangement 104 of FIG. 1 in further detail, in accordance with two embodiments, are shown. For the embodiment of FIG. 2a, arrangement 104 includes one or more "basic" allergen data collection units 202 and a companion base station 242, coupled to each other through communication link or links 262. Allergen data collection unit 202 includes filtering arrangements 204, sensor 206, analog-to-digital (AID) converter 208, data buffer 210, communication interface 212, and micro-controller 214, coupled to each other as shown. Base station 242 includes communication interface 244, data buffer 246, communication interface 248, and micro-controller 250, coupled to each other as shown.

Filtering arrangement 204 (of allergen data collection unit 202) is used to filter out large allergens in the ambient air that are not relevant to the issue of asthma trigger, allowing only allergens smaller than certain sizes that are relevant to the issue of asthma trigger to pass through. In one embodiment, filter arrangement 204 filters out allergens with sizes 5 micron or larger, allowing only allergens with sizes smaller than 5 micron to pass through. In one embodiment, filter arrangement 204 is a collection of successive filters. In other embodiments, filter arrangement 204 may be a cyclone separator, or a virtual impactor.

Sensor 206 (of allergen data collection unit 202) monitors and detects the amount of allergens present in the filtered air, and outputs signals representative of the amount detected. In one embodiment, sensor 206 is of the optical type, capable of detecting and outputting signals to denote the amount of allergens (smaller than 5 microns) in the filtered air. An example of such sensor is the GP2U06 High Sensitivity Dust Sensor available from Sharp Electronics Corporation of Camas, Wash. Other sensors or sensor modules with similar capability or built along similar principles may also be used.

Analog-to-digital (A/D) converter 208 digitizes the allergen level signals output by sensor 206, and data buffer 210 stores the digitized allergen data. Communication interface 212 facilitates provision of the buffered allergen data (via communication link or links 262) to base station 242 for transmission to air/asthma advice server 112. Micro-controller 214 controls the operation of these elements. A/D converter 208, data buffer 210, communication interface 212 and micro-controller 214 are intended to represent a broad range of these elements known in the art. For examples, data buffer 210 may be SRAM, DRAM, and memory of other like kinds, and micro-controller 214 may be 8-bit, 16-bit, or >16-bit micro-controller. Communication interface 212 may be a serial or parallel interface, a serial bus interface, a "harsh environment" wired network controller or a wireless transceiver. Examples of serial bus interfaces are bus interfaces designed for the Universal Serial Bus (USB) as specified by USB Specification R1.0, Jan. 15, 1996, or the "Firewire" serial bus as specified by IEEE 1394 High Performance Serial Bus. Examples of "harsh environment" network controllers are network controllers designed for the consumer electronics bus as specified by The CEBus Standard EIA-600, for phone line based networking (as AnyPoint™ Home Networking controllers available from Intel Corporation of Santa Clara, Calif.), or for power line based networking (as controllers available from Intelogis of American Fork, Utah). Examples of wireless transceivers are transceivers designed in accordance with the Draft Specification of Bluetooth: A Global Specification for Wireless Connectivity, promulgated by the Bluetooth Special Interest Group, and wireless network controllers designed in accordance with IEEE 802.11 Wireless LAN Standard.

Communication interface 244 (of base station 242) facilitates receipt of the collected allergen data (via communication links 262) from allergen data collection unit or units 202. Communication interface 244 is an interface of like kind that complements communication interface 212 (of allergen data collection unit 202). Similar to data buffer 210 (of allergen data collection unit 202), data buffer 246 (of base station 242) temporarily stores the received allergen data, and staged them for transmission to geographically removed air/asthma advice server 112. Communication interface 248 (of base station 242) facilitates the actual transmission to air/asthma advice server 112. Likewise, micro-controller 250 controls the operations of these elements. Again, data buffer 246, communication interface 248, and micro-controller 250 are intended to represent a broad range of these elements known in the art. Data buffer 246 may be SRAM, DRAM and memory of other like kinds, and micro-controller 250 may be 8-bit, 16-bit or >16-bit micro-controllers. Communication interface 248 may be a modem, an ISDN adapter, a DSL adapter and the like, depending on whether the communication link between base station 242 and air/asthma advice server 112 is a PSTN connection, an ISDN connection or a Digital Subscriber Line (DSL) connection, and so forth. Other communication interfaces consistent with the communication media may also be used.

As alluded to earlier in the description of communication interface 212 of allergen data collection unit 202, communication link 262 may be a wired or a wireless communication connection. In the case of a wired communication connection, link 262 may be a serial or a parallel link, a serial bus, as well as a "harsh environment" local area network segment, as set forth above. In the case of a wireless communication link, link 262 may be any one of the example wireless medium set forth above.

In alternate embodiments, base station 242 may be replaced with a computer, properly equipped with the dual communication interfaces. These alternate embodiments are particularly useful in a home or office settings where the required computer already exist, thereby advantageously allowing the patient client to leverage on his/her past equipment investment. Alternatively, in like manner, base station 242 may be replaced with a cell phone. Such alternate arrangement is particularly useful in the above described automobile or boat settings, where the patient client is already equipped with a cell phone, thereby also advantageously allowing the patient client to leverage on his/her past equipment investment.

The embodiment of FIG. 2b is a "full" function integrated embodiment of allergen detection arrangement 104. That is, the data collection unit and the base station transmission unit of FIG. 2a have been combined into a single unit, and additional functional units are provided. Thus, similar to the embodiment of FIG. 2a, under the embodiment of FIG. 2b, arrangement 104 still includes filter arrangement 272, allergen sensor 274 and A/D converter 276, performing like functions as described earlier. However, unlike the embodiment of FIG. 2a, a single communication interface 278, capable of directly facilitating provision of the buffered allergen data to the geographically removed air/asthma advice server, as opposed to the dual communicative interfaces and base station approach, is used instead. In other words, communication interface 278 is analogous to the communication interface of the base station of FIG. 2a, and the communication interface of the "basic" allergen data collection unit has been eliminated.

Additionally, arrangement 104 is further provided with peak flow meter 280, a spirometer 282, a thermometer 284, a humidity meter 286, and chemical sensors 288 to measure various asthma related metrics. Peak flow meter 280 measures peak expiratory flow rate of a patient client, whereas spirometer 282 measures the forced expiratory volume and other lung function metrics of a patient client. Thermometer 284 measures the temperature of the ambient air and humidity meter 286 measures the humidity of the ambient air. Chemical sensors 288 measure various gas levels, e.g. carbon monoxide, ozone, nitrogen dioxide, sulfur dioxide, and so forth. These elements are known in the art. Arrangement 104 also includes display and input interface 290 to interact with the patient client, to facilitate provisions of inputs from, and feedback to the patient client. Display and input interface 290 may be any end-user input/output device known in the art. Larger memory 292 and more powerful microprocessor 294 are provided to buffer allergen and other asthma related (like peak expiratory flow rate) data, and to control the operation of the various elements. For the illustrated embodiment, the various elements are coupled to each other through bus 296, which may be one or multiple buses bridged together. Bus 296 may be any one of a number of system or peripheral buses known in the art, such as the $I^2C$ bus, the ISA bus, the EISA bus, and the like.

Figure 3A:
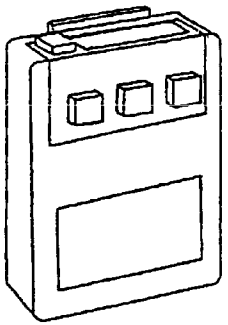
FIGS. 3a-3e illustrate air/asthma advice receipt arrangement of FIG. 1 in further detail, in accordance with two embodiments.
Figure 3B:
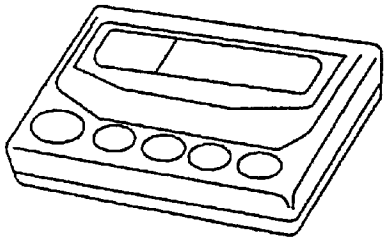

Referring now to FIGS. 3a-3e, wherein a number of example air/asthma advice receipt arrangements, suitable for use with the allergen detection arrangements of FIGS. 2a-2b, in accordance with a number of embodiments, are shown. FIG. 3a illustrates a conventional beeper known in the art. Under this embodiment, patient client 102 is provided with beeper, which in turn is employed by air/asthma advice server 112 to deliver a beeping signal to alert patient client 102 of an undesirable air/asthma condition. FIG. 3b illustrates a conventional pager known in the art. Under this embodiment, patient client 102 is provided with pager, which in turn is employed by air/asthma advice server 112 to page patient client 102 to call a particular telephone number for air or asthma advice, in view of an undesirable air/asthma condition.

Figure 3E:
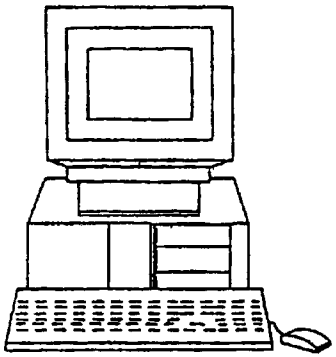
Figure 3D:
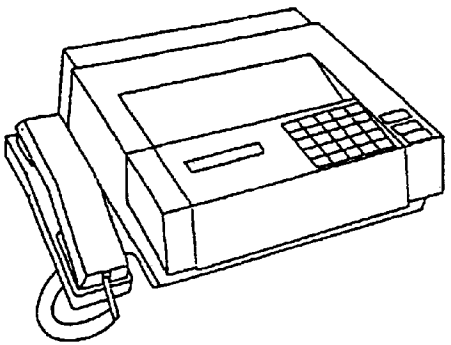
Figure 3C:
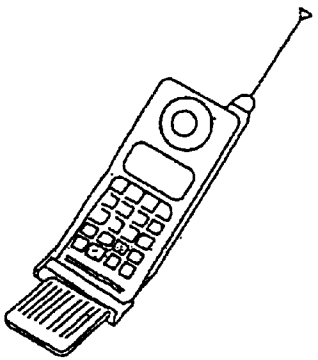

FIG. 3c illustrates a conventional PSTN or cellular telephone known in the art. Under this embodiment, patient client 102 is provided with telephone, which in turn is employed by air/asthma advice server 112 to deliver a verbal advice to patient client 102 in view of an undesirable air/asthma condition. If a cell phone is employed in lieu of base station 242 for allergen detection arrangement 104 (under the embodiment of FIG. 2a), phone may be the same phone. Air/asthma advice server 112 may wait till phone is not in use (e.g. not providing allergen data) before calling patient client 102 to provide the verbal advice.

FIG. 3d illustrates a conventional fax machine known in the art. Under this embodiment, patient client 102 is provided with fax machine, which in turn is employed by air/asthma advice server 112 to deliver a written advice to patient client 102 in view of an undesirable air/asthma condition. FIG. 3e illustrates a conventional computer (equipped with communication and email capability) known in the art. Under this embodiment, patient client 102 is provided with computer, which in turn is employed by air/asthma advice server 112 to deliver an electronic written advice to patient client 102 in view of an undesirable air/asthma condition. If a computer is employed in lieu of base station 242 for allergen detection arrangement 104 (under the embodiment of FIG. 2a), computer may be the same computer. For this embodiment, communication links 108 and 110 may be the same communication link.

Figure 4:
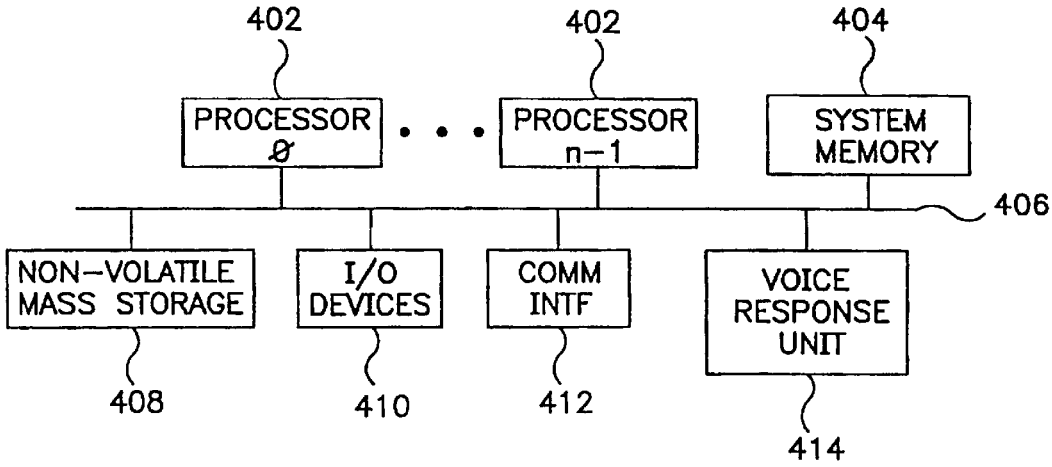
FIG. 4 illustrates an example server suitable for use to practice air/asthma advice server of FIG. 1, in accordance with one embodiment.

Referring now to FIG. 4, wherein a block diagram illustrating an example server suitable for use as air/asthma advice server 112 of FIG. 1, in accordance with one embodiment, is shown. As illustrated, server 400 includes a number of processors 402 and system memory 404 coupled to each other via system bus 406. System bus 406 is intended to represent a single bus implementation as well as a multi-bus implementation (where the buses are bridged together). Coupled to system bus 406 are non-volatile mass storage 408, such as hard disks, floppy disk, and so forth, input/output devices 410, such as keyboard, displays, and so forth, and communication interfaces 412, such as modem, ISDN adapters, DSL adapters, T1 DSU/CSU, cellular transceivers, satellite transceivers, Ethernet controllers, and so forth. For the illustrated embodiment, server 400 also includes voice response unit 414, which is also coupled to system bus 406. In alternate embodiments, server 400 may be a uni-processor system instead.

Each of these elements perform its conventional functions known in the art, i.e. processors 402 are used to execute programming instructions, system memory 404 and non-volatile mass storage 408 are used to store working and permanent copies of the programming instructions and data, and so forth. In particular, system memory 404 and non-volatile mass storage 408 are employed to store a working copy and a permanent copy of the programming instructions implementing air/asthma advice application 114 and patient client database 116. The constitution of elements 402-414 are well known, and accordingly, will not be further described.

Figure 5:
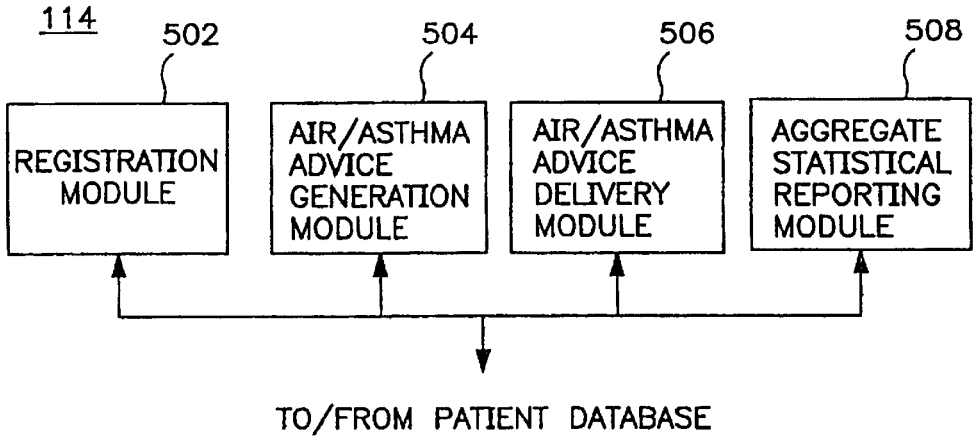
FIG. 5 illustrates the air/asthma advice application of FIG. 1 in further detail, in accordance with one embodiment.

Referring now to FIG. 5, wherein a block diagram illustrating air/asthma advice application 114 of FIG. 1 in further detail, in accordance with one embodiment, is shown. As illustrated, air/asthma advice application 114 includes registration module 502, air/asthma advice response generation module 504, and air/asthma advice delivery module 506. For the illustrated embodiment, air/asthma advice application 114 further includes aggregate statistical reporting module 508. These modules 502-508 are operationally "coupled" to each other and patient client database 116 as shown.

Registration module 502 is used to enroll and register patient client 102. In response to a registration request, registration module 502 creates a patient client record, along with the proper patient client information, to be described more fully below, in patient client database 116. For the illustrated embodiment, registration module 502 supports direct on-line registration by the patient client or the patient client's representative (in particular, through the Internet), as well as registration by an agent of the air/asthma advice server 112. Examples of the patient client's representative are the patient client's doctor, nurse, parent, guardian, and so forth, as described earlier.

Air/asthma advice generation module 504 is used to generate air/asthma advice for the patient clients, taking into consideration at least collected allergen data provided by the patient clients, and the air quality and related data for the surrounding areas of the allergen data collection locations. As described earlier, in response to the receipt of allergen data of a monitored location, generation module 504 retrieves air quality and related data from remote servers 122, and produces the air/asthma advice as set forth earlier.

For the illustrated embodiment, generation module 504 stores the advice generated for a patient client in an advice portion of the patient client's record in patient client database 116. Additionally, generation module 504 schedules the stored advice for delivery by delivery module 506. Scheduling is made by creating a delivery entry in a delivery job queue (not shown). Alternate approaches may also be employed.

For the illustrated embodiment, an identifier of the monitored location (e.g. a zip code, an identifier of a statistical metropolitan area, a telephone number area code, a global positioning coordinate, and so forth) may be dynamically provided along with the collected allergen data. However, an identifier of the patient client is always directly or indirectly provided (e.g. through a phone number or a unique network address of the patient client). If the identifier of the monitored location is not dynamically provided along with the collected allergen data, generated module 504 assumes the monitored location is a defaulted location (e.g. the patient client's home) previously identified and stored in patient client database 116, and retrieves the pre-stored default location identifier for the patient client accordingly.

For the illustrated embodiment, generation module 504 caches local copies for the air quality and related data for various surrounding areas. Accordingly, generation module 504 retrieves the air quality and related data for a surrounding area from the local cache, if the data are available locally and valid. Various application dependent validity policies, such as "not older than 7 days" or "not older than 24 hours" may be employed. That is, cache data are invalidated or considered to be invalid, once their "shelf lives" have exceeded the validity policy limits.

For the illustrated embodiment, generation module 504 also takes into consideration medical history of a patient client (including various allergen trigger thresholds), and employs artificial intelligence (AI) to generate the air/asthma advice responses. The precise policies to be employed for the AI reasoning portion of generation module 504 is application dependent. It may vary from a small set of simple rules to a large complex collection of interdependent rules.

Air/asthma advice delivery module 506 is used to make the actual delivery of the generated air/asthma advice to the patient clients (or their representatives, i.e. doctors, nurses, parents, guardians and so forth). As described earlier, the advice may be delivered in a variety of forms, beeping signals, pager messages, and so forth, and the patient clients may be equipped with different advice receipt arrangements. For the illustrated embodiment, delivery module 506 is equipped to support delivery in a wide range of forms, including in particular a beeping signal, a pager message, a voice message, a fax message, and an email. The preferred delivery form or forms of a patient client (and/or the representative) is pre-stored in a patient client database 116. In response to the scheduling of a delivery job, delivery module 506 ascertains the appropriate delivery form or forms for the advice, and makes the delivery accordingly.

In addition to the "push" model for delivering generated advice, delivery module 506 also supports a "pull" model for delivering generated advice. That is, delivery module 506 also "delivers" the generated advice to the patient client or his/her representative (e.g. doctor, nurse and so forth) in response to their queries (in particular, through the Internet).

Aggregated statistical reporting module 508 is used to compile and report on various advice related statistics. Examples of these aggregated statistics include cumulative exposures to indoor or outdoor allergens, correlation between individual or cumulative exposure data and lung function measurements, minimum, maximum, mean and standard deviation of exposure and lung function data by single and multiple unit dwellings and by geographical areas, multiple dwellings aggregated by common "medical" as well as non-medical characteristics, and so forth. The compiled statistics may be provided to interested third parties as well as operator of air/asthma advice server 112. Examples of interested third parties are educational and research institutions, pharmaceutical and medical device manufacturers, distributors and retailers, and marketing research organizations. For the illustrated embodiment, reporting module 508 supports batch delivery of the compiled statistics as well as on-line inquiry of the compiled statistics (in particular, through the Internet).

Modules 502-508 may be implemented in a variety of programming languages known in the art, including but not limited to, C, C++, Hypertext Markup Language (HTML), Java, JavaScript, and so forth.

Figure 6:
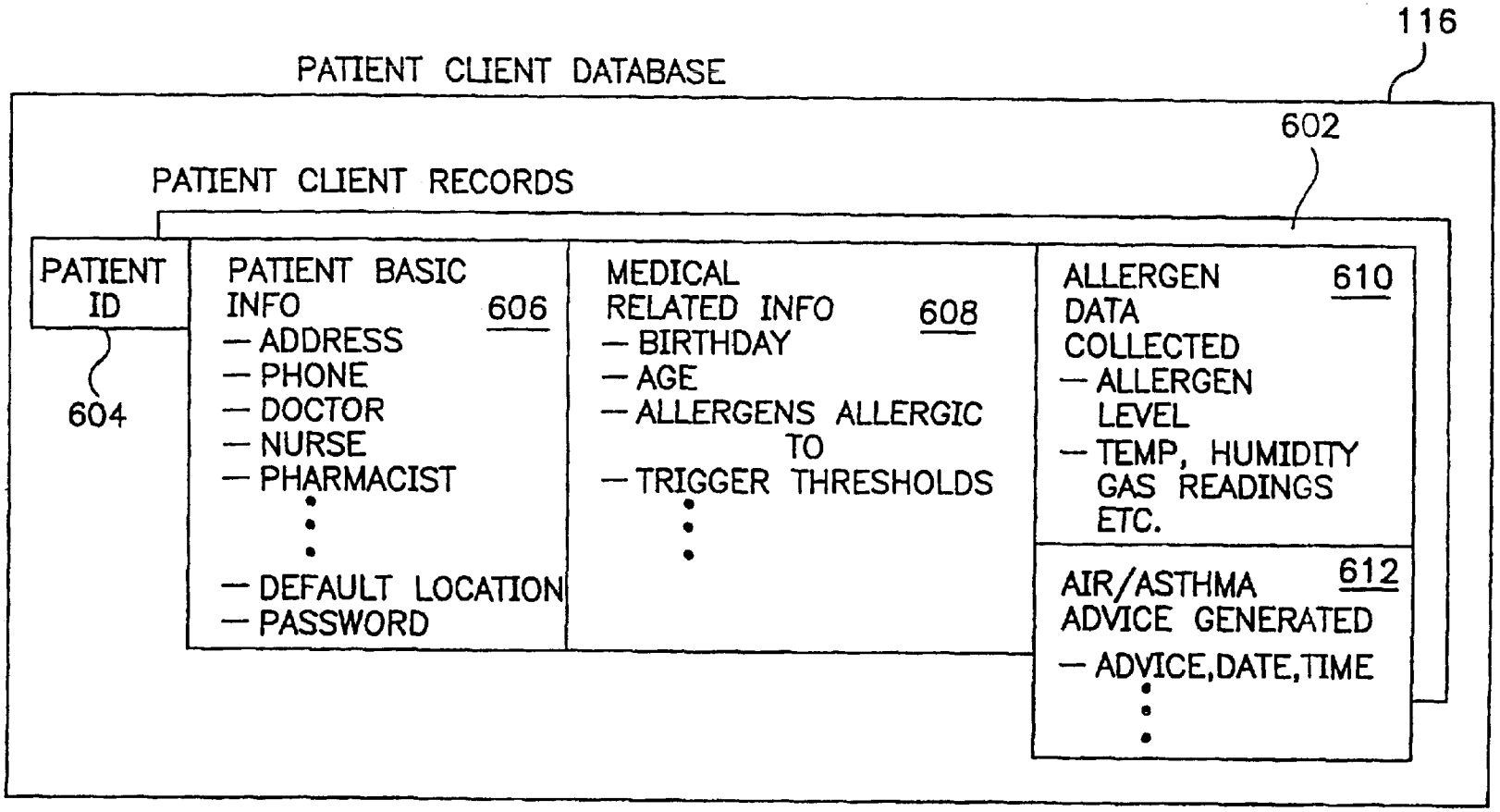
FIG. 6 illustrates the patient client database of FIG. 1 in further detail, in accordance with one embodiment.

Referring now to FIG. 6, wherein a block diagram illustrating patient client database 116 of FIG. 1 in further detail, in accordance with one embodiment, is shown. As illustrated, patient client database 116 includes various patient client records 602. Each patient client record 602 includes patient client identifier 604 identifying the patient client. In addition, each record 602 also includes basic information 606 about the patient client, medical related information 608 of the patient client, allergen data collected 610, and advice generated/delivered 612. Examples of basic information 606 include the patient client's address, phone number, doctor's name, address and phone number, pharmacist's name address and phone number, identifier and characteristics of the defaulted monitored location, password for accessing the patient client's information, and so forth. Where applicable, it may also include parent or guardian information. Examples of medical related information 608 include the patient client's birthday, age, allergens allergic to, trigger thresholds for various allergens and related matters, medication currently taking, and so forth. Allergen data collected 610 includes related data such as temperature, humidity, level of various gases in the ambient air, as well as in some embodiments, the patient clients' peak expiratory flow rate, and forced expiratory volume. Air/asthma advice generated/delivered 612 includes the advice, and the date and time the advice are generated and delivered, as well as to whom and in what form the advice were delivered.

Figure 7:
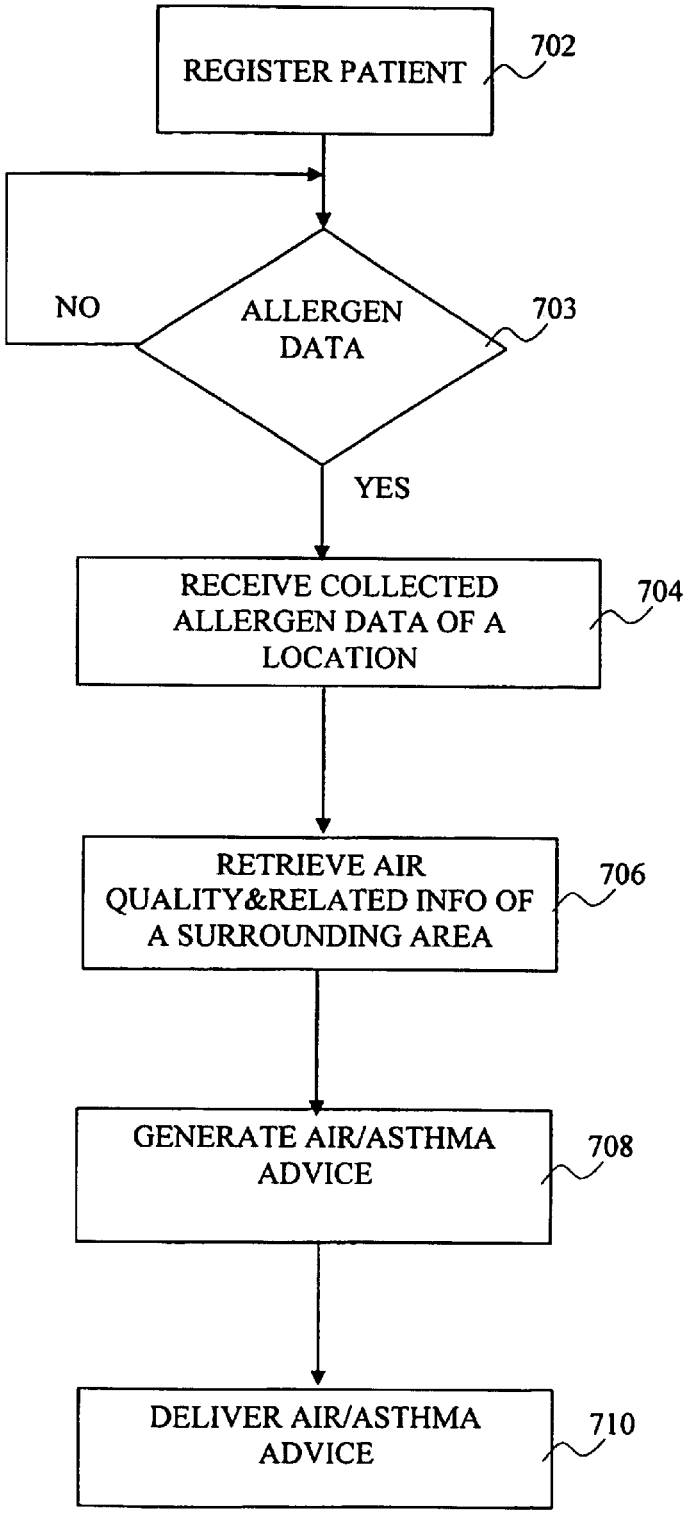
FIG. 7 illustrates an air/asthma advice method of the present invention, in accordance with one embodiment.

Referring now to FIG. 7, wherein a flow chart summarizing an air/asthma advice method of the present invention, in accordance with one embodiment, is shown. As illustrated, at 702, a patient client is registered or enrolled with an operator of the air/asthma advice server described earlier, resulting in the creation of a patient client record in the patient client database for the patient client. The registration may be made by the patient client or a representative (doctor, nurse, and so forth) on behalf of the patient client. The registration may be made directly on-line or by an agent of the operator.

At 704, a registered patient client, using an allergen detection arrangement, provides collected allergen data for a monitored location to the air/asthma advice server. The monitored location may be a default location, or a temporal location (dynamically identified for the air/asthma advice server). At 706, air/asthma advice server retrieves air quality and related data for a general area surrounding the monitored location. The data are either retrieved from local cached copies or directly from remote servers (operated by various public or private institutions). At 708, air/asthma advice server generates air/asthma advice for the patient client based at least on the allergen data provided and the air quality and related data retrieved. In one embodiment, the air/asthma advice is generated based also on the medical history of the patient client.

At 710, performed immediately or in due course, the air/asthma advice server delivers the air/asthma advice for the patient client. The delivery may be made to the patient client and/or his/her representative, in one or more of a number of forms, as described earlier.

Epilogue

Various embodiments for methods and apparatuses for detecting allergen and generating/providing air/asthma advice for patient clients have been described. Those skilled in the art will recognize that the present invention is not limited by the embodiments and their detail described, instead, the present invention can be practiced with modifications and alterations within the spirit and scope of the appended claims. The description is thus to be regarded as illustrative instead of restrictive on the present invention.

What is claimed is:

1. A method comprising:

receiving particulate data collected at an interior location;

retrieving air quality data for an exterior surrounding area of the interior location *from a remote server*; and generating a particulate advice response for a client situated at the interior location, based at least in part on the combination of the received particulate data of the interior location and the retrieved air quality data of the exterior surrounding area.

2. The method of claim 1, wherein said particulate data comprises data for particulate with sizes smaller than 5 micron.

3. The method of claim 1, wherein said receiving comprises receiving said particulate data of the interior location through a data connection.

4. The method of claim 3, wherein said data connection is established over a communication media selected from a group consisting of a Public Switching Telephone Network (PSTN) connection, an Integrated Digital Service Network (ISDN) connection, and an Internet connection.

5. The method of claims 1, wherein said air quality data comprises data selected from a group consisting of ozone, oxides of nitrogen, oxides of sulphur, photochemical smog, humidity, temperature, barometric air pressure, pollen level, occurrence of sandstorm, occurrence of tornado, occurrence of forest fire, occurrence of agricultural burning.

6. The method of claim 1, wherein said retrieving comprises retrieving said air quality data from a remote server through a data connection.

7. The method of claim 6, wherein said remote server is a server maintained by an entity selected from a group consisting of a government agency, a hospital, a university, a research institution, a news reporting organization, and a commercial air quality reporting service.

8. The method of claim 6, wherein said data connection is established over a communication media selected from a group consisting of a Public Switching Telephone Network (PSTN) connection, an Integrated Digital Service Network (ISDN) connection, a Frame Relay connection, an Asynchronous Transfer Mode (ATM) connection, and an Internet connection.

9. The method of claim 1, wherein said particulate advice response comprises a response selected from a group consisting of an indoor air quality advisory, an outdoor air quality advisory, a weather advisory, and a natural/mad-made pollution event advisory.

10. The method of claim 1, wherein the method further comprises delivering the generated particulate advice response on behalf of the client to an associated recipient selected from a group consisting of a medical physician, a nurse, a pharmacist, a parent and a guardian of the client.

11. The method of claim 10, wherein said generated particulate advice response being delivered to the associated recipient in a form selected from a group consisting of beeping signal, a pager message, a voice message, a faxed report, and an e-mail message.

12. The method of claim 10, wherein said delivery being made to the associated recipient through a communication link selected from a group consisting of a wired and a wireless communication link.

13. The method of claim 1, wherein said receiving further comprises receiving additional data selected from a group of consisting of lung function data of the client, ambient temperature of the interior location, humidity at the interior location, and concentration of a gas at the interior location, and said particulate advice response is generated based also on said received additional data.

14. The method of claim 13, wherein said additional data being collected contemporaneously with said particulate data.

15. The method of claim 1, wherein said particulate advice response is generated based also in part on particulate triggering threshold(s).

16. The method of claim 15, wherein said particulate trigger thresholds being provided by one selected from a group consisting of the client, a medical physician of the client and a nurse of the client.

17. The method of claim 1, wherein said retrieving further comprises retrieving weather data of the surrounding area, and said particulate advice response is generated based also on said retrieved weather data.

18. The method of claim 17, wherein said weather data being retrieved from a remote server of a weather monitoring and reporting service.

19. The method of claim 1, wherein the method further comprises compiling aggregated statistical data on said generation of particulate advice response for a plurality of clients.

20. The method of claim 19, wherein the method further comprises providing said compiled aggregated statistical data to a recipient selected from a medical research organization, a product marketing organization, a product manufacturer, a product distributor, and a product retailer.

21. An apparatus, comprising:

a processor;

at least one communication interface coupled to the processor; and a storage medium coupled to processor and having stored therein a first, a second, and a third plurality of programming instructions to be executed by the processor to receive particulate data collected at an interior location, to retrieve air quality data for an exterior surrounding area of the interior location from a remote server, and to generate a particulate advice response for a client situated in the interior location, based at least in part on the combination of the received particulate data of the interior location and the retrieved air quality data of the exterior location.

22. The apparatus of claim 21, wherein said at least one communication interface comprises at least one communication interface selected from a group consisting of a local area networking (LAN) interface, a Public Switching Telephone Network (PSTN) interface, an Integrated Digital Service Network (ISDN) interface, a T1 line interface, a cellular transceiver interface, and a satellite transceiver interface.

23. The apparatus of claim 21, wherein said storage medium further having pre-stored therein said air quality data.

24. The apparatus of claim 21, wherein said storage medium further having stored therein a fourth plurality of programming instructions to be executed by the processor to deliver the generated particulate advice response to a recipient in a form selected from a group consisting of a beeping signal, a pager message, a voice message, a faxed report, and an e-mail message.

25. The apparatus of claim 22, wherein said apparatus further comprises a voice response unit for constituting said generated particulate advice response in said voice message form.

26. The apparatus of claim 21, wherein said first plurality of programming instructions are also to be executed by the processor to receive additional data selected from a group of consisting of lung function data of the client, ambient temperature of the interior location, humidity at the interior location, and concentration of a gas at the interior location, and said third plurality of programming instructions in generating said particulate advice response further base said generation on said received additional data.

27. The apparatus of claim 21, wherein said third plurality of programming instructions in generating said particulate advice response further base said generation on particulate triggering threshold(s).

28. The apparatus of claim 21, wherein said second plurality of programming instructions are also to be executed by the processor to retrieve weather data of the surrounding area, and said third plurality of programming instructions in generating said particulate advice response further base said generation on said retrieved weather data.

29. The apparatus of claim 21, wherein said storage medium further having stored therein a fourth plurality of programming instructions to be executed by the processor to compile aggregated statistical data on said generation of particulate advice response for a plurality of clients.

30. The apparatus of claim 29, wherein said storage medium further having stored therein a fifth plurality of programming instructions to be executed by the processor to provide said compiled aggregated statistical data to a recipient selected from a medical research organization, a product marketing organization, a product manufacturer, a product distributor, and a product retailer.

*31. A method comprising:*

*collecting particulate data at a site using one or more sensors locally disposed at the site;*

*accessing a wireless local area network medium at the site, the wireless local area network medium coupled with a public network disposed off-site;*

*sending the collected particulate data to a remote server coupled to the public network, via the wireless local area network medium; and*

*receiving particulate advice response, from the remote server, that is based at least in part upon the collected particulate data and air quality data for an exterior surrounding area of the site.*

*32. The method of claim 34, further comprising:*

*receiving the collected particulate data from the one or more sensors at a base station coupled to the local area network medium; and*

*sending the collected particulate data to the remote server from the base station.*

*33. A system comprising:*

*one or more data collection units coupled to a local area network at a site, at least one of the one or more data collection units having a particulate sensor to collect particulate data at the site;*

*a base station coupled to the local area network and a public network, to receive the particulate data from the one or more data collection units via the local area network and to send the collected particulate data to a server, which is at a location remote from the site, via the public network; and*

*an advice receipt arrangement at the site to receive advice from the server via the public network, said advice based at least in part upon the collected particulate data.*

*34. A method comprising:*

*receiving air quality data collected at an interior location defined at least in part by a structure;*

*receiving structure data related to the structure; and*

*generating an advice response based at least in part on a combination of the received air quality data and the received structure data.*

*35. The method of claim 34, wherein said receiving structure data further comprises receiving data related to at least construction or location of the structure.*

*36. The method of claim 34, further comprising:*

*receiving data on air quality for an exterior surrounding area of the structure; and*

*generating the advice response based at least in part on a combination of the air quality data collected at the interior location, air quality data for the exterior surrounding area, and the structure data.*

*37. A system comprising:*

*a collection arrangement configured to collect air quality data at an interior location defined at least in part by a structure; and*

*an advice generation module configured to*

*receive the collected air quality data;*

*receive structure data related to the structure; and*

*generate an advice response based at least in part on a combination of the received air quality data and the received structure data.*

*38. The system of claim 37, wherein the collection arrangement comprises:*

*at least two sensors selected from a particulate sensor, a chemical sensor, a temperature sensor, and a humidity sensor to collect the air quality data.*

*39. The system of claim 37, wherein the advice generation module is further configured to:*

*receive data on air quality for an exterior surrounding area of the structure; and*

*generate the advice response based at least in part on a combination of the air quality data collected at the interior location, data on air quality for the exterior surrounding area, and the structure data.*

*40. A machine accessible medium having instructions stored thereon, which, when accessed, results in a machine:*

*receiving air quality data collected at an interior location defined at least in part by a structure;*

*receiving structure data related to the structure; and*

*generating an advice response based at least in part on a combination of the received air quality data and the received structure data.*

*41. The machine accessible medium of claim 40, wherein said receiving of air quality data further comprises:*

*receiving at least data relating to particulates, temperature, humidity, or gas levels.*

*42. A method comprising:*

*receiving air quality data collected at an interior location defined at least in part by a structure;*

*receiving client data related to a condition of a client associated with the structure; and*

*generating an advice response based at least in part on a combination of the received air quality data and the received client data.*

*43. The method of claim 42, wherein said receiving client data further comprises:*

*receiving medical data of the client.*

*44. The method of claim 42, further comprising:*

*receiving structure data; and*

*generating the advice response based at least in part on a combination of the received air quality data, the received client data, and the received structure data.*

*45. The method of claim 42, further comprising:*

*receiving data on air quality for an exterior surrounding area of the structure; and*

*generating the advice response based at least in part on a combination of the received air quality data collected at the interior location, the received client data, and the received data on air quality for the exterior surrounding area.*

* * * * *